(12) United States Patent
Ong et al.

(10) Patent No.: US 7,507,281 B2
(45) Date of Patent: Mar. 24, 2009

(54) ANTIMICROBIAL CEMENTITIOUS COMPOSITION, METHOD AND ARTICLE

(75) Inventors: Ivan W. Ong, Charlotte, NC (US); H. Wayne Swofford, Newton, NC (US)

(73) Assignee: Microban Products Company, Huntersville, NC (US)

(*) Notice: Subject to any disclaimer, the term of this patent is extended or adjusted under 35 U.S.C. 154(b) by 0 days.

(21) Appl. No.: 11/754,832

(22) Filed: May 29, 2007

(65) Prior Publication Data
US 2007/0281096 A1    Dec. 6, 2007

Related U.S. Application Data

(63) Continuation-in-part of application No. 11/219,251, filed on Sep. 2, 2005, now Pat. No. 7,223,443.

(51) Int. Cl.
| C04B 24/12 | (2006.01) |
| C04B 103/67 | (2006.01) |
| C04B 103/69 | (2006.01) |
| A01N 33/00 | (2006.01) |
| B05D 5/00 | (2006.01) |
| B05D 7/00 | (2006.01) |

(52) U.S. Cl. ............... 106/18.32; 106/15.05; 106/725; 106/727; 106/808; 427/372.2; 514/396

(58) Field of Classification Search ............ 106/18.32, 106/808, 15.05, 18.33, 18.34, 18.35, 18.36, 106/725, 727; 427/372.2; 514/396
See application file for complete search history.

(56) References Cited

U.S. PATENT DOCUMENTS

| 4,944,892 | A | * | 7/1990 | Leathers et al. | ............. 510/199 |
| 6,440,440 | B1 | * | 8/2002 | Meerpoel et al. | ............. 424/405 |
| 7,223,443 | B2 | * | 5/2007 | Ong | ............. 427/372.2 |
| 2006/0009535 | A1 | * | 1/2006 | Wantling | ............. 516/43 |
| 2006/0283356 | A1 | * | 12/2006 | Donlon et al. | ............. 106/660 |

FOREIGN PATENT DOCUMENTS

WO    WO 2006/021556 A1 * 3/2006

\* cited by examiner

*Primary Examiner*—Anthony J Green
(74) *Attorney, Agent, or Firm*—Cliff D. Weston

(57) ABSTRACT

An antimicrobial cementitious composition for imparting antimicrobial characteristics to cement comprises a cement-based compound and an imazalil agent; combinations of agents also may be employed.

19 Claims, 3 Drawing Sheets

ANTIMICROBIAL CEMENTITIOUS COMPOSITION, METHOD AND ARTICLE

CROSS-REFERENCE TO RELATED APPLICATION

This application is a continuation-in-part of and claims priority from U.S. Ser. No. 11/219,251, now U.S. Pat. No. 7,223,443, filed on Sep. 2, 2005, the contents of which are incorporated herein for all purposes.

FIELD OF THE INVENTION

The present invention relates to antimicrobial cementitious compositions, and in particular to antimicrobial cementitious compositions and methods for producing and using same.

BACKGROUND OF THE INVENTION

Cementitious compositions have been used in the construction industry for years. Examples of cementitious compositions include cement, concrete, mortar, grout, and stucco. Stucco is commonly used in the construction of buildings, particularly on the exterior of a building as a siding treatment. A framework such as paper or metal wire conventionally is affixed to a building, for example, and stucco is applied to the framework. Stucco is typically comprised of cement and inert materials such as sand and lime.

A common problem with a cementitious composition such as stucco is that it has a high pH in its wet-mix phase or when newly applied. A high pH (e.g., greater than 9) intrinsically protects against microorganisms and will naturally protect the material from fungi and other microbial colonization. The cementitious composition is gradually neutralized over time, however, and the untreated cementitious composition loses this innate efficacy against microorganisms such as bacteria, algae, mold and fungus. Furthermore, stucco is porous and absorbs moisture, which is particularly attractive to microorganisms.

Grout commonly finds applications in shower and tub enclosures. Moisture conditions facilitate growth of mold and other undesirable microbial growth, marring the appearance of the shower/tub area and causing malodor.

Previous attempts have been made to add antimicrobial agents to cementitious compositions. However, there are problems that have yet to be solved with known antimicrobial cementitious compositions.

The high pH of cementitious compositions places unique demands on the particular choice of an antimicrobial agent. Since the pH of a cured cementitious composition tends to remain very high even after it sets, the particular antimicrobial agent chosen must be very resistant to chemical degradation due to the high pH. Some antimicrobial agents such as triclosan are also particularly sensitive to the combination of high pH and ultraviolet light, such that the antimicrobial agent causes yellowing when the two conditions are present.

Other attempts have focused on the addition of antimicrobial agents to various components added to cementitious compositions, such as fibers (added for strength) or lightweight particles (added to reduce overall density of the cured cementitious article). For example, U.S. Pat. No. 6,162,845 discloses the use of triclosan in fibers for blending with concrete and like materials.

However, this approach adds complexity, as the antimicrobial agent must be engineered to remain durably affixed to the added component while still being available to provide antimicrobial efficacy. Doped additional components then also becomes a required component, adding material and expense.

Another problem with many known antimicrobial agents is that they disrupt the cure chemistry of a cementitious composition. For example, certain antimicrobial agents may be susceptible to coupling with impurities and will lead to possible color changes.

Still another problem with many known antimicrobial agents is that they have poor solubility in a cementitious composition. The agents may leach out of the cementitious composition over time and/or upon exposure to conditions typical of the use environment. Also as a result of poor solubility, some antimicrobial agents cannot be homogeneously distributed within the finished cementitious substrate.

DETAILED DESCRIPTION OF PREFERRED EMBODIMENT(S)

Figure 1:
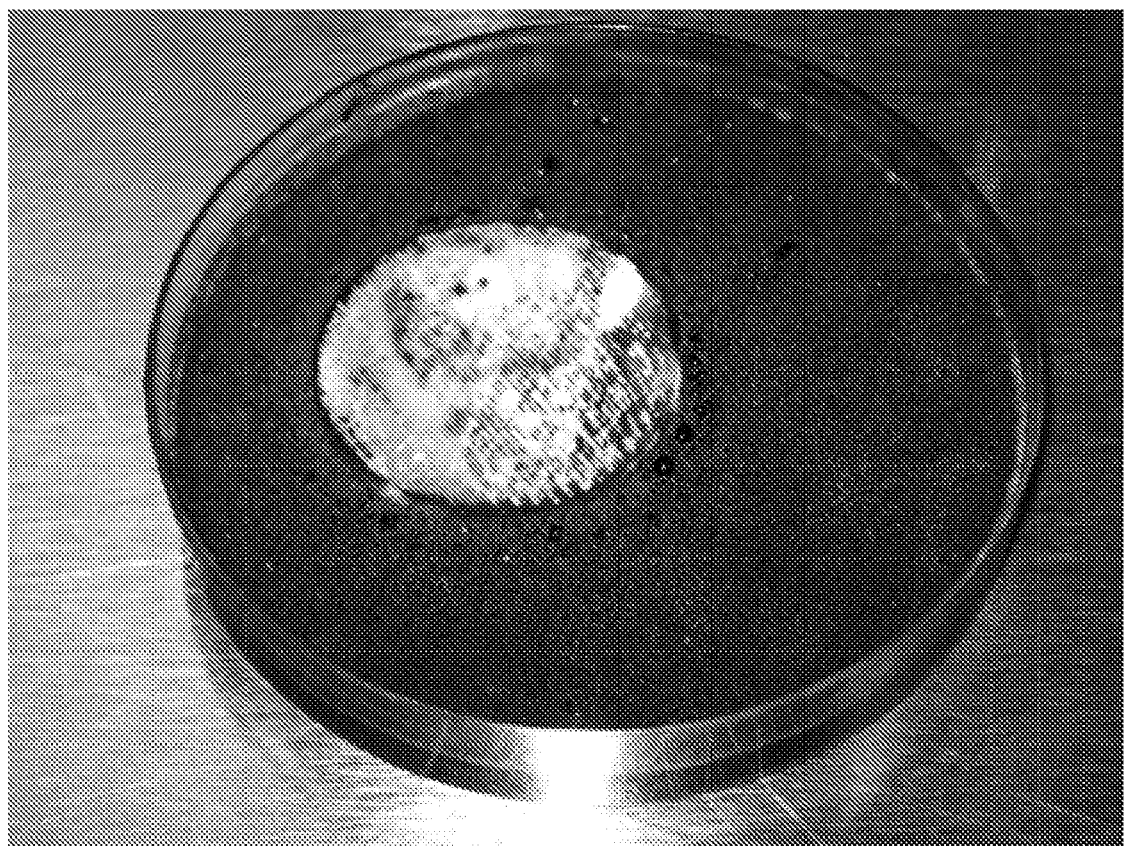
FIGS. 1-3 are black-and-white photographs of sample and control grout discs after inoculation and challenge with *Aspergillus niger*.

In this document, certain terms such as antimicrobial, antibacterial, antifungal, microbistatic, cement, cementitious, and the like may be used. While not intended to be limiting, the following definitions are provided as an aid to the reader.

The term "antimicrobial" as used herein includes biostatic activity, i.e., where the proliferation of microbiological species is reduced or eliminated, and true biocidal activity where microbiological species are killed. Furthermore, the terms "microbe" or "antimicrobial" should be interpreted to specifically encompass bacteria and fungi as well as other single-celled organisms such as mold, mildew and algae.

The term "cement" as used herein refers to a commonly known building material comprising powdered materials which develop strong adhesive qualities when combined with water. Cement generally is a dry powder made of a mixture of calcined limestone, silica, alumina, lime, iron oxide, magnesia and clay, typically used with water and sand or gravel to make concrete and mortar.

The term "cementitious" as used herein refers to the presence of cement. A cementitious composition comprises cement but also may further comprise inert materials such as sand and lime. "Cement" as used herein may further comprise other additives such as stabilizers, durability enhancers, colorants, viscosity modifiers, and the like.

Examples of cementitious compositions include, but are not limited to, concrete, grout, mortar and stucco. A preferred cementitious composition is stucco, which typically is comprised of cement and sand. Stucco generally is commercially available in a premixed form.

The following description of the preferred embodiment(s) is merely exemplary in nature and is in no way intended to limit the antimicrobial cementitious composition, its application, or uses.

The antimicrobial cementitious premix compound as disclosed herein has antimicrobial activity and is comprised of a cementitious material and the antimicrobial agent Additive IF4 (Microban Products Company, Huntersville, N.C.). The Additive IF4 formulation contains the active ingredient (±)-1-[2-(2,4-dichlorophenyl)-2-(2-propenyloxy)ethyl]-1H-imidazole (CAS No. 73790-28-0), commonly known as imazalil (Jannsen Pharmaceutica, Belgium) and having the structure:

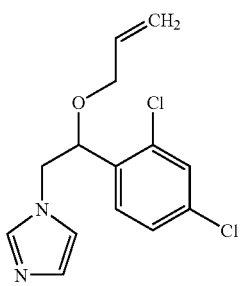

Especially favored is (±)-1-[2-(2,4-dichlorophenyl)-2-(2-propenyloxy)ethyl]-1H-imidazole sulfate (CAS No. 58594-72-2). Imazalil and imazalil sulfate are referred to collectively herein as "imazalil agent".

In one embodiment, an antimicrobial cementitious composition for imparting antimicrobial characteristics to a cement-based composition comprises a cementitious premix compound and imazalil agent. Imazalil agent solubilizes very efficiently in aqueous grout and cementitious mixes.

This species also appears to be thermally stable up to 160° C. and above. Thermal stability makes imazalil agent especially well-suited for inclusion in the production of cementitious powder by various manufacturers, as these powders are typically dried and packed at elevated temperatures. Many other antimicrobial/antifungal agents tend to discolor and clump when so thermally exposed.

The imazalil agent has proven to be UV stable and exhibits no discoloration after prolonged exposure to ultraviolet irradiation (UVA 340 lamps, 168 hrs). Resistance to ultraviolet radiation and discoloring is advantageous given the typical outdoor environment of cured cementitious articles.

In another embodiment, a method of making an aqueous antimicrobial cementitious composition includes combining a quantity of imazalil agent with cement-based compound(s) to form an antimicrobial cementitious composition. The weight concentration of antimicrobial agent in the cementitious composition can be as low as about 250 ppm, based upon the weight of the cementitious composition. A practical upper end to the useful concentration range is about 5000 ppm. However, it is within the scope of the present method to use concentrations of antimicrobial agents greater than 5000 ppm, if specific cement-based compounds and other factors so warrant.

In preferred embodiments, the combined weight concentration of the antimicrobial agent in the cementitious composition is in a range from about 750 ppm to about 3500 ppm based upon the weight of the cementitious composition. More preferred embodiments utilize a range from about 900 ppm to about 2500 ppm.

A method for making an antimicrobial cementitious composition comprises the steps of combining, e.g. by admixture, a quantity of imazalil agent with cement-based compound to form an antimicrobial cementitious composition wherein the combined weight concentration of the antimicrobial agent in the cementitious composition is at least about 250 ppm based upon the weight of the cementitious composition.

In an embodiment wherein the cementitious composition is a dry premix. In a second embodiment, the cementitious composition is a liquid premix dissolved in an aqueous solvent (e.g. water). The cementitious composition can be stucco or grout mix.

The uniquely high pH of cementitious systems places unique demands on the particular choice of an antimicrobial agent. As the pH of a cured cementitious system tends to remain very high even after it sets, the particular antimicrobial agent chosen must be very resistant to hydrolysis at the high pH. If the antimicrobial agent is susceptible to hydrolysis, then it would be most likely be quickly degraded. Some antimicrobial agents such as triclosan are also particular sensitive to exposure to ultraviolet light such as from sunlight and high pH, and such antimicrobial agents will yellow when the two elements are present.

As stated above, a preferred antimicrobial agent for use in the antimicrobial cementitious composition of the present disclosure is imazalil agent. For example, imazalil agent satisfactorily addresses this stability requirement as it has outstanding high pH stability and can successfully endure the wet-phase cement mixing and curing steps. Moreover, imazalil agent does not disrupt the cure chemistry of the cementitious composition and seems to have no effect on the setting time.

A third embodiment is a solid-phase cured cementitious article having persistent antimicrobial properties. This embodiment comprises a cured cement-based compound and imazalil agent, the latter in a concentration of from at least about 250 ppm based on the weight of the cement-based compound in its premix form.

While fresh cementitious/stucco compositions have a high intrinsic pH that will naturally protect the material from micro-organism attack, with time, the structure will gradually lose its intrinsic high pH due to atmospheric neutralization. However, imazalil agent has an optimal combination of stability and solubility in the cementitious composition. It does not dissolve out of stucco at neutral to acidic pHs as its solubility in that range is very low. Additionally, this agent is not easily leached out of cured, solid-phase stucco or grout. Imazalil agent is not degraded by neutral or acidic rain water.

Thus, due to its excellent combination of low leach and good stability, imazalil agent is an excellent antimicrobial agent for use in the antimicrobial cementitious composition, as it is very easy to add to stucco and dissolves rapidly into a slurry mix. Thus, the protection provided by imazalil agent is expected to be durably present long after the intrinsic pH-mediated protection has waned.

Stucco that is affixed to the exterior surface of a house is very usually painted. While possible fungicides in the paints protect the exterior surface, antimicrobial agents incorporated into the cementitious material itself offer excellent overall protection to the entire stucco structure. There is beneficial protection provided by the antimicrobial agents disclosed herein, as moisture may leach and promote fungal growth from within the wall outwards (e.g., water leaks and/or seepage through seams or flaws in the surface). Furthermore, the implemented imazalil agent is better retained within the cementitious composition in a conventionally installed and painted stucco exterior treatment, as the exterior paint coating acts as a barrier to the elements and possible leaching.

In an alternative embodiment, the present composition can contain a second antimicrobial agent in addition to the imazalil agent. For example, chlorothalonil or 2,4,5,6-Tetrachloroisophthalonitrile (CAS No. 1897-45-6) is commercially available under the trade name MICROBAN ADDITIVE M15™ (Microban Products Company, Huntersville, N.C.).

As used herein the term "azoles" should be interpreted to include any of the "azole" antimicrobial agents known to those skilled the art. Preferred azoles include, but are not limited to, thiabendazole, propiconazole, tebuconazole, and mixtures thereof.

Another preferred oxathiazine is bethoxazin commercially available under the trade name MICROBAN ADDITIVE GBF™ (Microban Products Company, Huntersville, N.C.).

Ttriamine diamines suitable for use as the second antimicrobial agent include, but are not limited to, 1,3,5-triazine-2,4-diamine, cyclopropyl-N'-(1,1-dimethylethyl)-6-(methylthio)-1,3,5-triazine-2,4-diamine, commercially available as MICROBAN ADDITIVE IA1™ (Microban Products Company, Huntersville, N.C.).

A preferred ortho-phenyl phenol is sodium orthophenyl phenol (NaOPP) which is commercially available under the trade name MICROBAN ADDITIVE P2™ (Microban Products Company, Huntersville, N.C.).

For ease of discussion, the above chemicals are collectively referred to herein as "antimicrobial agents." One criterion in the selection of an antimicrobial agent as used in the practice of the present composition is that it be efficacious at commercially acceptable concentrations; in other words, that the efficacious agent concentration be commercially cost-permissive and not cause undue harm to the surface to which it is affixed or to the environment.

EXAMPLE 1

An 80 lb bag of BAL grout compound was obtained. Additive IF4, comprising imazalil sulfate, was admixed to the dry grout compound at levels sufficient to provide active agent concentrations of 1000 ppm (0.1%) and 2000 ppm (0.2%), each based upon the total weight of the dry admixture. A batch of dry admixture weighing 200 grams was used to form discs or "pucks". Water was added (32 g) according to packaging instructions, after which the mix was thoroughly mixed before being cast into round molds of approximately 1.5 inches diameter.

In addition, an untreated set of samples prepared according to packaging instructions was cast as control for testing comparison.

Following the neutralization treatment, the samples initially were plated against *Aspergillus niger* (a common household black mold) using the AATCC 30 Part III test. The 30 Part III test is an aggressive 7-day antifungal evaluation in which the test samples are exposed to high levels of fungal spores and incubated under optimal conditions (elevated temperatures and humidity) for the spores to germinate.

At the end of the 7-day incubation period, the test plates were removed from the test chamber and the samples were evaluated for fungal attack and encroachment. The results of the evaluation are shown in Table 1.

TABLE 1

| Sample | Zone of Inhibition, mm | | Growth |
|---|---|---|---|
| Imazalil Sulfate, ppm | K. pneumoniae | S. aureus | A. niger |
| 0 (Control) | 4 | 7 | NO |
| 500 | 5 | 5 | NO |
| 1000 | 5 | 6 | NO |
| 2000 | 5 | 6 | NO |

That the negative controls also show zones of inhibition and lack of *A. niger* growth is surprising. The alkaline nature of freshly cured grout articles, discussed above, confer an intrinsic but transient antimicrobial property thereto. The pH decreases and the native antimicrobial effect dissipates over time, as the cementitious article is subjected to typical use environments such as a shower or tub enclosure, residential building exterior, and the like.

EXAMPLE 2

Grout samples were prepared and cured as in Example 1, with antimicrobial agent admixed into the dry compound at levels of 0 ppm, 1000 ppm, and 2000 ppm based upon the total weight of the dry mix and antimicrobial agent (excluding water). Water was added, the slurry mixed, and 1.5-inch diameter pucks cast.

After air-curing, the samples were exposed for eight hours in either of QUV/Spray Accelerated Weathering Controller or Xenon Testing Chamber Xe-3HS (both by Q-Panel Lab Products, Cleveland, Ohio). The QUV exposure is an assay well known in the art for simulating aging, discoloration and/or degradation caused by conditions of ultraviolet radiation exposure, such as would be encountered in an outdoor application.

Thereafter, the sample discs were subjected to one hour of water spray, followed by one hour of condensation, alternatingly repeated for a total of eight hours. This treatment neutralizes the pH of the grout samples, simulating brief real-world exposure of the grout articles to, e.g., a shower stall application.

Samples then were plated against *Aspergillus niger* using the 30 Part III test. At the end of the 168-hour incubation period, the test plates were removed from the test chamber and the samples were evaluated for fungal attack and encroachment. The antimicrobial agent tested and the results of the evaluation are shown in Table 2; control and experimental plates are shown in FIGS. 1-3.

*A. niger* was observed to grow in the control plate medium and on the cementitious sample (FIG. 1). Compared to the lack of growth observed on the negative control of Example 1, this sample demonstrates the readily impermanent character of the pH-based antimicrobial effect inherent in fresh cementitious articles.

Figure 2:
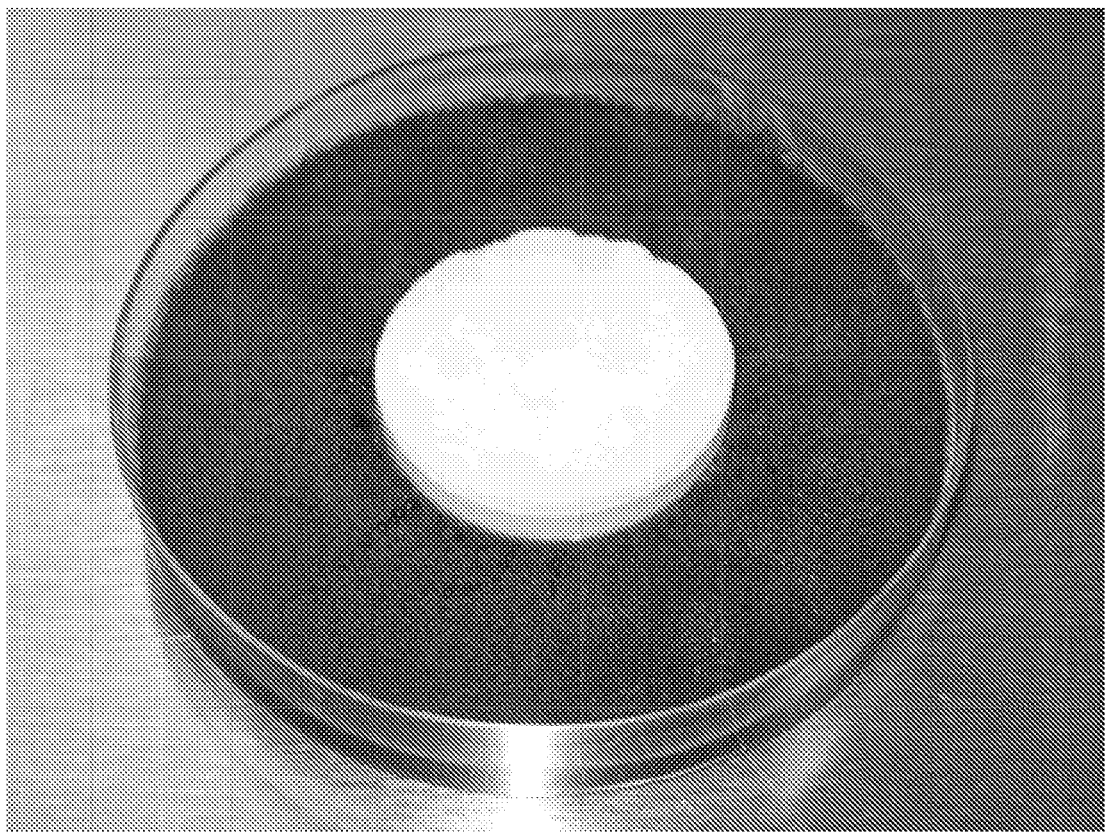
Figure 3:
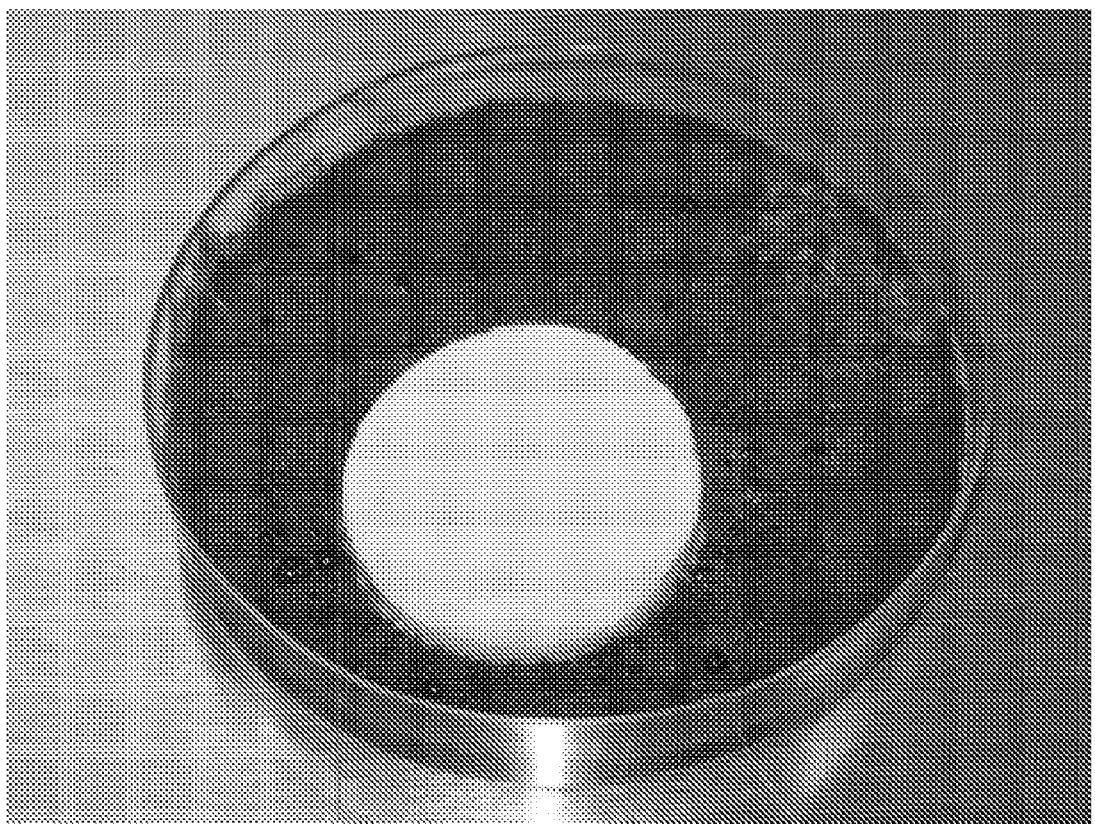

In sharp contrast, no growth was observed on the neutralized cementitious sample pucks having 1000 ppm or 2000 ppm imazalil sulfate incorporated therein (FIGS. 2-3). Having accounted for any pH-mediated antimicrobial property via serial washing, we conclude that the imazalil agent in the pucks prevents *A. niger* growth thereon.

TABLE 2

| Sample Imazalil Sulfate, ppm | Growth A. niger |
|---|---|
| 0 (Control) | YES |
| 1000 | NO |
| 2000 | NO |

FIG. 1 is a photograph of an untreated grout sample that was exposed to *Aspergillus niger*. The fungus appears to have encroached upon the edges and exposed major face of the grout disc sample, which shows initial signs of growth. The untreated sample appears to offer little resistance to fungal attack.

FIG. 2 is a photograph of a BAL grout sample at 1000 ppm of imazalil agent. At 1000 ppm, the grout puck offers strong resistance to fungal attack, with the exposed major surface retaining its pristine white appearance.

FIG. 3 is a photograph of a BAL grout puck at 2000 ppm of imazalil agent. At 2000 ppm, the grout sample appears to offer significant disruption to fungal encroachment in its immediate vicinity.

It will therefore be readily understood by those persons skilled in the art that the present composition and methods are susceptible of broad utility and application. Many embodiments and adaptations other than those herein described, as well as many variations, modifications and equivalent arrangements, will be apparent from or reasonably suggested to one of ordinary skill by the present disclosure and the foregoing description thereof, without departing from the substance or scope thereof. Accordingly, while the present composition and methods have been described herein in detail in relation to its preferred embodiment, it is to be understood that this disclosure is only illustrative and exemplary and is made merely for purposes of providing a full and enabling disclosure. The foregoing disclosure is not intended or to be construed to limit or otherwise to exclude any such other embodiments, adaptations, variations, modifications and equivalent arrangements.

What is claimed is:

1. A pre-cured antimicrobial cementitious composition, comprising:
   a cement-based compound; and
   a first antimicrobial agent consisting essentially of a salt of an imazalil agent present in an amount of from about 250 ppm to about 4000 ppm based on the weight of the cement-based compound.

2. The composition of claim 1 wherein the first antimicrobial agent is present in an amount from about 750 ppm to about 3000 ppm based on the weight of the cement-based compound.

3. The composition of claim 1 wherein the pre-cured composition is a cement premix, concrete premix, mortar premix, grout premix, or stucco premix.

4. The composition of claim 1 wherein the antimicrobial cementitious composition further includes a second antimicrobial agent selected from the group consisting of an orthophenyl phenol, an an orthophenyl phenol salt, a tolyl diiodomethyl sulfone, a zinc pyrithione, an oxathiazine, an azole, a chlorothalonil, and a triazine diamine.

5. A method of making a pre-cured antimicrobial cementitious composition, comprising:
   combining a quantity of a first antimicrobial agent consisting essentially of a salt of an imazalil agent with a quantity of a pre-cured cement-based compound to form a pre-cured cementitious composition;
   wherein the weight concentration of first antimicrobial agent in the cementitious composition is from at least about 250 ppm to about 4000 ppm based upon the weight of the pre-cured cement-based compound.

6. The method of claim 5 wherein the first antimicrobial agent is combined in an amount from 500 ppm.

7. The method of claim 5 wherein the pre-cured antimicrobial cementitious composition is a cement mix, a concrete mix, a mortar mix, a grout mix, or a stucco mix.

8. The method of claim 5, further comprising:
   combining with a quantity of a pre-cured cement-based compound a second antimicrobial agent selected from the group consisting of an orthophenyl phenol, an an orthophenyl phenol salt, a tolyl diiodomethyl sulfone, a zinc pyrithione, an oxathiazine, an azole, a chlorothalonil, and a triazine diamine.

9. A method for making a cured antimicrobial cementitious article, comprising:
   affixing a pre-cured antimicrobial cementitious composition to a substrate, wherein the pre-cured antimicrobial cementitious composition includes:
   a cement-based compound, and
   first antimicrobial agent consisting essentially of a salt of an imazalil agent,
   wherein the first antimicrobial agent is present in the pre-cured antimicrobial cementitious composition at a concentration of at least about 250 ppm to about 4000 ppm based on the weight of the cement-based compound; and
   curing the affixed antimicrobial cementitious composition.

10. The method of claim 9 wherein the first antimicrobial agent is present in an amount from 500 ppm.

11. The method of claim 9 wherein the pre-cured antimicrobial cementitious composition is a cement mix, a concrete mix, a mortar mix, a grout mix, or a stucco mix.

12. The method of claim 9 wherein the antimicrobial cementitious composition further includes a second antimicrobial agent selected from the group consisting of an orthophenyl phenol, an an orthophenyl phenol salt, a tolyl diiodomethyl sulfone, a zinc pyrithione, an oxathiazine, an azole, a chlorothalonil, and a triazine diamine.

13. A method for making an antimicrobial solid cementitious article, comprising:
   affixing an antimicrobial cementitious composition to a substrate, said antimicrobial cementitious composition including a salt of an imazalil agent present in an amount of from at least about 500 ppm to about 4000 ppm based on the weight of the cementitious composition; and
   dehydrating said affixed composition.

14. The method of claim 13 wherein the salt of an imazalil agent is present in an amount from about 750 ppm to about 2000 ppm based on the weight of the cement-based compound.

15. The method of claim 13 wherein the cementitious composition is stucco.

16. The method of claim 13 wherein the antimicrobial cementitious composition further includes an antimicrobial agent selected from the group consisting of a tolyl diiodomethyl sulfone, a zinc pyrithione, an oxathiazine, a chlorothalonil, and a triazine diamine.

17. The method of claim 13 wherein the antimicrobial cementitious composition is selected from the group consisting of a concrete composition, a mortar composition, a grout composition, and a stucco composition.

18. The method of claim 13 wherein the antimicrobial cementitious composition is in a liquid state.

19. The method of claim 13 wherein the substrate is a substantially vertically oriented substrate.

* * * * *